United States Patent
Cao et al.

(10) Patent No.: US 11,179,196 B2
(45) Date of Patent: Nov. 23, 2021

(54) MEDICAL SYSTEMS AND METHODS FOR MODULATING NERVES

(71) Applicant: Boston Scientific Scimed, Inc., Maple Grove, MN (US)

(72) Inventors: Hong Cao, Maple Grove, MN (US); Huisun Wang, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/872,290

(22) Filed: Jan. 16, 2018

(65) Prior Publication Data
US 2018/0154166 A1 Jun. 7, 2018

Related U.S. Application Data

(62) Division of application No. 14/194,570, filed on Feb. 28, 2014, now abandoned.
(Continued)

(51) Int. Cl.
*A61B 18/12* (2006.01)
*A61B 18/14* (2006.01)
(Continued)

(52) U.S. Cl.
CPC ............ *A61B 18/1492* (2013.01); *A61N 5/00* (2013.01); *A61B 18/1206* (2013.01);
(Continued)

(58) Field of Classification Search
CPC ........ A61B 17/320068; A61B 18/1206; A61B 18/1233; A61B 18/1492; A61B 18/16; A61B 18/1815; A61B 2018/00375; A61B 2018/00434; A61B 2018/00547; A61B 2018/00577; A61B 2018/00642; A61B 2018/00702; A61B 2018/00815; A61B 2018/00821; A61B 2018/00827;
(Continued)

(56) References Cited

U.S. PATENT DOCUMENTS 3,579,042 A * 5/1971 Abend .................. H02H 7/205
361/54
3,963,030 A * 6/1976 Newton ................. A61B 18/12
606/40
(Continued)

FOREIGN PATENT DOCUMENTS

JP    H07509147 A    10/1995
JP    2001519199 A    10/2001
(Continued)

*Primary Examiner* — Michael F Peffley
*Assistant Examiner* — Amanda L Zink
(74) *Attorney, Agent, or Firm* — Kacvinsky Daisak Bluni PLLC

(57) ABSTRACT

Medical devices and methods for making and using medical devices are disclosed. An example medical device may include a medical device for modulating nerves. The medical device may include an elongate shaft having a distal region. Two or more electrodes may be positioned adjacent to the distal end region of the elongate shaft. A control unit may supply power and control algorithms to the electrodes. The control algorithm may allow the electrodes to be operated simultaneously and individually.

20 Claims, 6 Drawing Sheets

Related U.S. Application Data

(60) Provisional application No. 61/777,744, filed on Mar. 12, 2013.

(51) Int. Cl.
| | |
|---|---|
| *A61N 5/00* | (2006.01) |
| *A61B 18/18* | (2006.01) |
| *A61B 18/00* | (2006.01) |
| *A61B 18/16* | (2006.01) |
| *A61B 90/00* | (2016.01) |

(52) U.S. Cl.
CPC .......... *A61B 18/1233* (2013.01); *A61B 18/16* (2013.01); *A61B 18/1815* (2013.01); *A61B 2018/00375* (2013.01); *A61B 2018/00434* (2013.01); *A61B 2018/00547* (2013.01); *A61B 2018/00577* (2013.01); *A61B 2018/00642* (2013.01); *A61B 2018/00702* (2013.01); *A61B 2018/00815* (2013.01); *A61B 2018/00821* (2013.01); *A61B 2018/00827* (2013.01); *A61B 2018/00875* (2013.01); *A61B 2018/141* (2013.01); *A61B 2018/1467* (2013.01); *A61B 2090/065* (2016.02); *A61B 2090/3966* (2016.02)

(58) Field of Classification Search
CPC .... A61B 2018/00875; A61B 2018/141; A61B 2018/1467; A61B 2090/065; A61B 2090/3966; A61N 1/36014; A61 5/00
See application file for complete search history.

(56) References Cited

U.S. PATENT DOCUMENTS

| | | | | |
|---|---|---|---|---|
| 4,918,745 A * | 4/1990 | Hutchison | .......... | A61N 1/36038 455/41.2 |
| 5,540,681 A * | 7/1996 | Strul | ................ | A61B 18/1206 606/1 |
| 5,782,827 A * | 7/1998 | Gough | ................ | A61B 18/18 606/41 |
| 5,784,244 A * | 7/1998 | Moran | ................ | H01H 47/10 361/152 |
| 6,152,882 A * | 11/2000 | Prutchi | ............... | A61B 5/0422 600/509 |
| 6,299,574 B1 * | 10/2001 | Ochs | ................ | A61N 1/3937 600/7 |
| 6,430,446 B1 * | 8/2002 | Knowlton | ........... | G06F 16/9017 607/101 |
| 7,623,929 B1 * | 11/2009 | Griffith | ............... | A61N 1/3787 607/57 |
| 9,180,005 B1 | 11/2015 | Lashinski et al. | | |
| 9,314,644 B2 * | 4/2016 | Wu | ........... | A61F 7/007 |
| 2005/0240239 A1 * | 10/2005 | Boveja | ................ | A61N 7/022 607/40 |
| 2008/0255642 A1 * | 10/2008 | Zarins | ............... | A61B 18/1206 607/99 |
| 2008/0275316 A1 * | 11/2008 | Fink | ...................... | A61B 5/442 600/306 |
| 2008/0281310 A1 * | 11/2008 | Dunning | ............. | A61N 1/0408 606/32 |
| 2008/0281311 A1 * | 11/2008 | Dunning | ............... | A61B 18/16 606/32 |
| 2010/0145410 A1 * | 6/2010 | Kirsch | ............. | A61N 1/36025 607/45 |
| 2011/0270066 A1 * | 11/2011 | Gregory | ................ | A61B 5/053 600/373 |
| 2012/0323237 A1 * | 12/2012 | Paul | .................... | A61B 18/1206 606/41 |
| 2013/0304052 A1 * | 11/2013 | Rizq | ..................... | A61B 18/18 606/33 |
| 2016/0151109 A1 * | 6/2016 | Buck | ...................... | A61N 1/056 606/35 |

FOREIGN PATENT DOCUMENTS

| | | |
|---|---|---|
| JP | 2010511469 A | 4/2010 |
| JP | 2012135613 A | 7/2012 |
| JP | 2014510563 A | 5/2014 |
| JP | 2015500696 A | 1/2015 |
| WO | 2011126580 A2 | 10/2011 |
| WO | 2012015722 A1 | 2/2012 |
| WO | 2012174375 A1 | 12/2012 |
| WO | 2013030743 A1 | 3/2013 |

\* cited by examiner

MEDICAL SYSTEMS AND METHODS FOR MODULATING NERVES

CROSS-REFERENCE TO RELATED APPLICATIONS

This application is a divisional application of U.S. application Ser. No. 14/194,570, now abandoned, filed Feb. 28, 2014, the entirety of which is incorporated herein by reference, which claims priority under 35 U.S.C. § 119 to U.S. Provisional Application Ser. No. 61/777,744, filed Mar. 12, 2013, the entirety of which is incorporated herein by reference.

TECHNICAL FIELD

The present disclosure pertains to medical devices, and methods for using medical devices. More particularly, the present disclosure pertains to elongated medical devices for modulating nerves.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include a medical device for modulating nerves. The medical device may include an elongated shaft having a proximal end and a distal end. Two or more electrodes may be positioned adjacent to the distal end of the elongate shaft. The medical device may further include a ground pad and a control unit in electrical communication with each of the two or more electrodes. The control unit may be positioned adjacent to the proximal end of the elongate shaft and may be configured to selectively control power applied to the electrodes. The control unit may allow the electrodes to be simultaneously powered or powered individually, as desired.

An example use of an example medical device may include a method for performing nerve modulation. The method may include providing a nerve modulation system. The nerve modulation system may include an elongate shaft having a proximal end and a distal end and two or more electrodes positioned adjacent to the distal end of the elongate shaft. The nerve modulation system may further include at least one temperature sensor positioned adjacent to each of the two or more electrodes and a ground pad. A control unit including a controller and a radiofrequency generator may be positioned adjacent to the proximal end of the elongate shaft. The nerve modulation system may be advanced through a lumen such that the two or more electrodes are adjacent to a target region. Power may then be applied at a predetermined maximum power to the two or more electrodes. A temperature adjacent to each of the two or more electrodes may be measured. The impedance between each of the two or more electrodes and the ground pad may also be monitored. The control unit may include a control algorithm for controlling a power level and a duration power is applied to each of the two or more electrodes and discontinuing power to at least one of the two or more electrodes when the at least one electrode achieves a predetermined modulation criteria.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
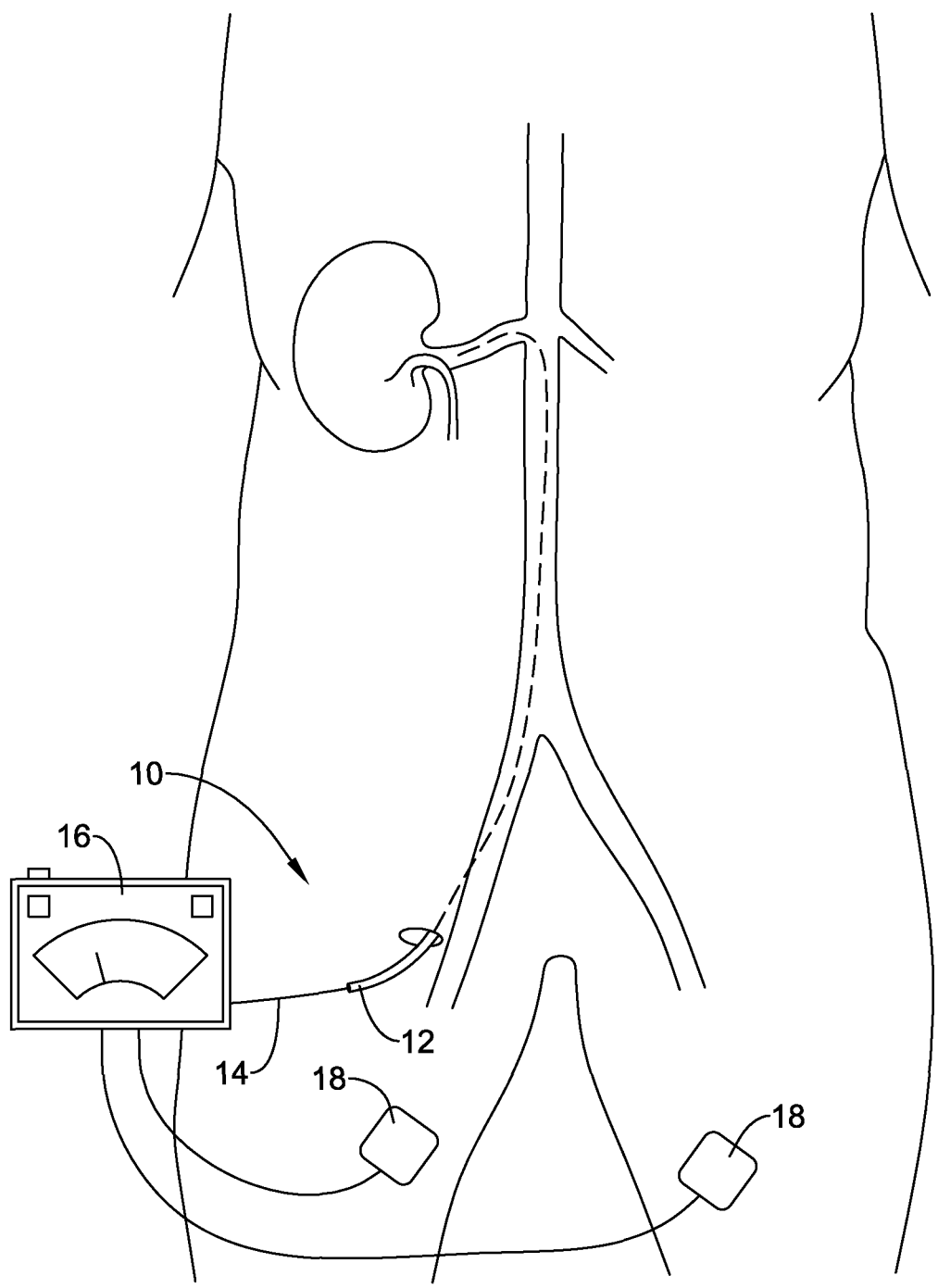
FIG. 1 is a schematic view illustrating a renal nerve modulation system in situ.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Certain treatments require the temporary or permanent interruption or modification of select nerve function. One example treatment is renal nerve ablation, which is sometimes used to treat conditions related to hypertension, congestive heart failure, diabetes, or other conditions impacted by high blood pressure or salt retention. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

While the devices and methods described herein are discussed relative to renal nerve modulation, it is contemplated that the devices and methods may be used in other treatment locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, cardiac ablation, pulmonary vein isolation, tumor ablation, benign prostatic hyperplasia therapy, nerve excitation or blocking or ablation, modulation of muscle activity, hyperthermia or other warming of tissues, etc. In some instances, it may be desirable to ablate perivascular renal nerves with radiofrequency ablation.

Some ablation devices may be provided with multiple electrodes or modulation elements. Multi-electrode catheters may be powered such that all electrodes are activated simultaneously (single-shot) or the electrodes are activated sequentially one after another (multi-shot). In a single-shot application, radiofrequency (RF) power may be delivered to all of the electrodes at the same time. It is contemplated that in a single-shot application, the electrodes may also be directly connected on one another. A single-shot device may treat each electrode equally and thus cannot adjust power to specific electrodes to address issues such as electrode-to-tissue contact or underlying tissue structure and/or properties. Multi-shot devices may deliver RF power to one electrode at a time and may generate lesions sequentially. This may take longer to complete an ablation procedure than a single-shot device and may lengthen the procedure time. Further, while an RF generator may be designed to have multiple channels, each configured to power an individual electrode, there may be challenges to separating the channels in frequency or interference of electrical current distribution when all of the channels are powered simultaneously. It may be desirable to have a device which can perform ablation in both a single-shot mode and a sequential mode without the use of separate channels.

FIG. 1 is a schematic view of an illustrative renal nerve modulation system in situ. System 10 may include one or more conductive element(s) 16 for providing power to a renal ablation system including a renal nerve modulation device 12 and, optionally, within a delivery sheath or guide catheter 14. A proximal end of conductive element(s) 16 may be connected to a control and power unit 18, which may supply the appropriate electrical energy to activate one or more electrodes disposed at or near a distal end of the renal nerve modulation device 12. In addition, control and power unit 18 may also be utilized to supply/receive the appropriate electrical energy and/or signal to activate one or more sensors disposed at or near a distal end of the renal nerve modulation device 12. When suitably activated, the electrodes are capable of ablating tissue as described below and the sensors may be used to sense desired physical and/or biological parameters. The terms electrode and electrodes may be considered to be equivalent to elements capable of ablating adjacent tissue in the disclosure which follows. In some instances, return electrode patches 20 may be supplied on the legs or at another conventional location on the patient's body to complete the circuit. A proximal hub (not illustrated) having ports for a guidewire, an inflation lumen and a return lumen may also be included.

The control and power unit 18 may include monitoring elements to monitor parameters such as power, voltage, pulse size, temperature, force, contact, pressure, impedance and/or shape and other suitable parameters, with sensors mounted along renal nerve modulation device 12, as well as suitable controls for performing the desired procedure. In some embodiments, the power unit 18 may control a radiofrequency (RF) electrode. The electrode may be configured to operate at a suitable frequency and generate a suitable signal. It is further contemplated that other ablation devices may be used as desired, for example, but not limited to resistance heating, ultrasound, microwave, and laser devices and these devices may require that power be supplied by the power unit 18 in a different form.

Figure 2:
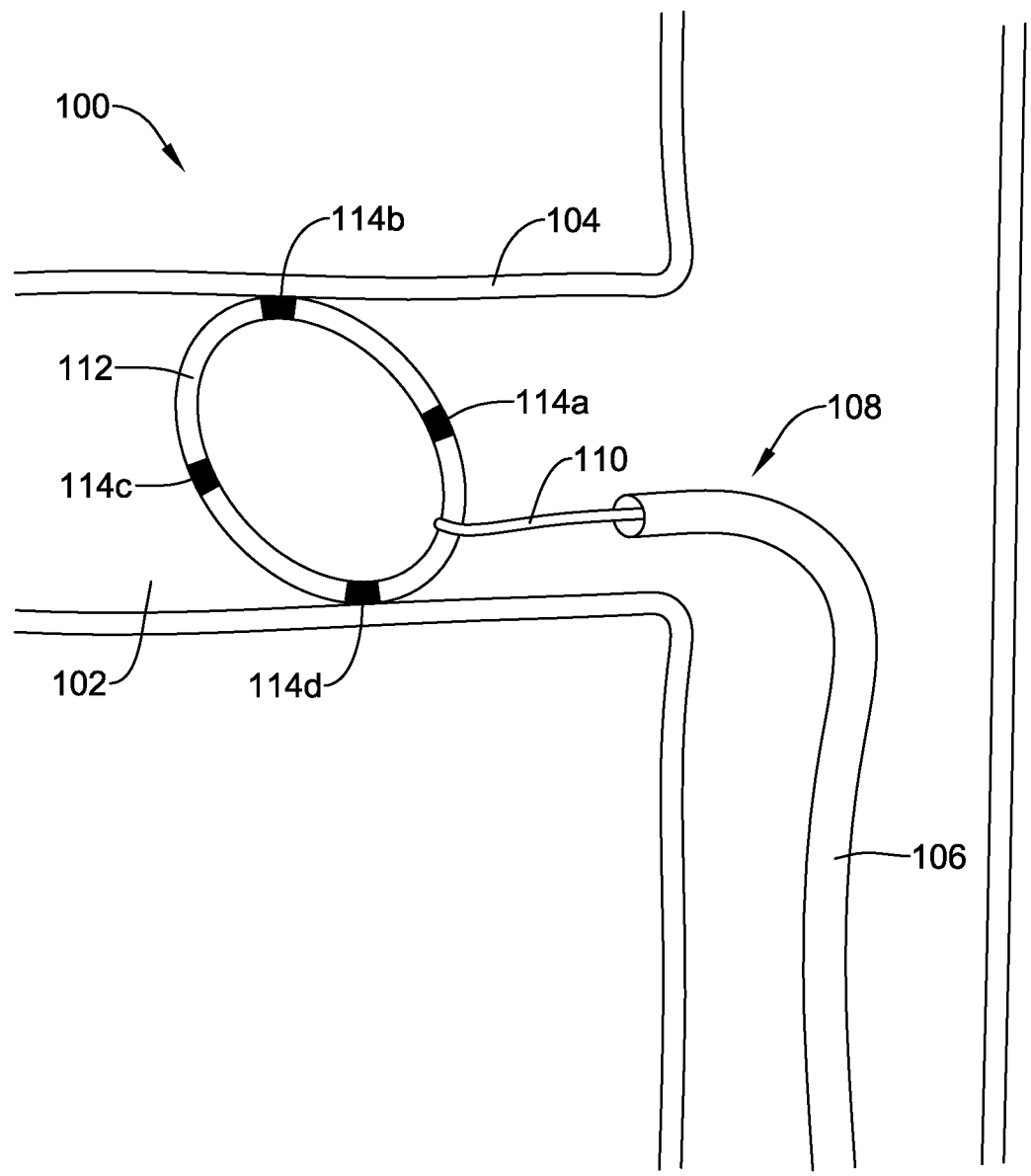
FIG. 2 is an illustrative multi-electrode nerve modulation system.

FIG. 2 is an illustrative embodiment of a distal end of a renal nerve modulation system 100 that may be utilized to ablate or otherwise modulate renal nerves while minimizing damage to surrounding tissue. As shown, the renal nerve modulation system 100 may be disposed within a body lumen or vessel 102 having a wall 104. The outer surface of the vessel wall 104 may be surrounded by local body tissue. The local body tissue may comprise adventitia and connective tissues, nerves, fat, fluid, etc. in addition to the muscular vessel wall 104. The system 100 may include a catheter shaft 106 having a distal end region 108. The catheter shaft 106 may extend proximally from the distal end region 108 to a proximal end configured to remain outside of a patient's body. The proximal end of the catheter shaft 106 may include a hub attached thereto for connecting other treatment devices or providing a port for facilitating other treatments. It is contemplated that the stiffness of the catheter shaft 106 may be modified to form a modulation system 100 for use in various vessel diameters and various locations within the vascular tree. In some instances, the proximal portion of the catheter shaft 106 may be flexible to enable consistent torque transmission. The catheter shaft 106 may further include one or more lumens extending therethrough. For example, the catheter shaft 106 may include a guidewire lumen and/or one or more auxiliary lumens. The lumens may have a variety of configurations and/or arrangements. For example, the guidewire lumen may extend the entire length of the catheter shaft 106 such as in an over-the-wire catheter or may extend only along a distal portion of the catheter shaft 106 such as in a single operator exchange (SOE) catheter. These examples are not intended to be limiting, but rather examples of some possible configurations. While not explicitly shown, the modulation system 100 may further include temperature sensors/wire, an infusion lumen, radiopaque marker bands, fixed guidewire tip, a guidewire lumen, external sheath and/or other components to facilitate the use and advancement of the system 100 within the vasculature. It is further contemplated that the modulation system 100 may include one or more centering baskets, expandable framework, and/or expandable balloons to center or otherwise position the modulation system 100 within the body lumen 102. In some embodiments, the catheter shaft 106 may include push and/or pull wires to deflect a distal end region 108 of the catheter shaft 106. For example, a push and/or pull wire may be attached adjacent to the distal end of the catheter shaft 106 and then extend along an outer surface of the catheter shaft 106 or along an interior passageway formed in the shaft 106 to a position where it is accessible to a user. In other embodiments, the catheter shaft 106 may incorporate a planar deflection mechanism, such as a rib and spine mechanism. However, it is contemplated that the catheter shaft 106 may be deflected in any desired manner.

The system 100 may include an elongate member 110 extending within a lumen of the catheter shaft 106. In some instances, the elongate member 110 may extend the entire length of the catheter shaft 106 while in other instances, the elongate member 110 may be attached to the catheter shaft 106 adjacent the distal end region 108 thereof. In some instances, the distal end region 112 of the elongate member 110 may form a ring or lasso type structure. The distal end region 112 may be configured to be advanced to the desired treatment region within the catheter shaft 106. Once adjacent to the desired treatment region, the distal end region 112 of the elongate member 110 may be advanced distally such that it exits the lumen of the catheter shaft 106. In some instances, the distal end region 112 may be configured to self-expand from a collapsed position into a ring while in other instances, actuation mechanisms may be employed to expand the distal end region 112. It is contemplated that the distal end region 112 may form a unitary structure with the elongate member 110. In other instances, the distal end region 112 may be formed of a separate structure and fixedly secured to the elongate member 110.

The system 100 may include one or more distal ablation electrodes 114a, 114b, 114c, 114d (collectively 114) positioned adjacent the distal end region 112 of the elongate member 110. While the ablation electrodes 114 are described as radiofrequency electrodes, it is contemplated that other methods and devices for raising the temperature of the nerves may be used, such as, but not limited to: ultrasound, microwave, or other acoustic, optical, electrical current, direct contact heating, or other heating. While the system 100 is illustrated as including four ablation electrodes 114, it is contemplated that the modulation system 100 may include any number of ablation electrodes 114 desired, such as, but not limited to, one, two, three, or more. The ablation electrodes 114 may be longitudinally and/or radially and/or circumferentially spaced as desired. The ablation electrodes 114 may be spaced about the distal end region 112, although this is not required. In some instances, the electrodes 114 may be positioned about the distal end region 112 such that not all of the electrodes 114 contact the vessel wall 104 simultaneously when the distal end region 112 is in the expanded state. In other instances, the electrodes 114 may be arranged such that all of the electrodes 114 are configured to contact the vessel wall 104 simultaneously when the distal end region 112 is in the expanded state.

In some embodiments, the electrodes 114 may include wire wrapped coils, generally solid shapes, ball-type electrodes, etc. In some embodiments, the ablation electrodes 114 may be formed of a separate structure and attached to the distal end region 112. For example, the ablation electrodes 114 may be machined or stamped from a monolithic piece of material and subsequently bonded or otherwise attached to the distal end region 112. In other embodiments, the ablation electrodes 114 may be formed directly on the surface of the distal end region 112. For example, the ablation electrodes 114 may be plated, printed, or otherwise deposited on the surface. It is contemplated that the ablation electrodes 114 may take any shape desired, such as, but not limited to, square, rectangular, circular, elliptical, etc. In some instances, the ablation electrodes 114 may be a radiopaque marker band. The ablation electrodes 114 may be formed from any suitable material such as, but not limited to, platinum, gold, stainless steel, cobalt alloys, or other non-oxidizing materials. In some instances, titanium, tantalum, or tungsten may be used.

While not explicitly shown, the ablation electrodes 114 may also include other structures and/or features associated typically associated with ablation (e.g., thermal ablation) such as a temperature monitoring member, which may take the form of a thermocouple or thermistor. In at least some embodiments, a thermistor including two thermistor wires may be disposed adjacent to one or more of the ablation electrodes 114. In some embodiments, the wires are not physically connected to ablation electrodes 114.

The modulation system 100 may be advanced through the vasculature in any manner known in the art. For example, system 100 may include a guidewire lumen to allow the system 100 to be advanced over a previously located guidewire. In some embodiments, the modulation system 100 may be advanced, or partially advanced, within a guide catheter such as the guide catheter 16 shown in FIG. 1. Once the ablation electrodes 114 of the modulation system 100 have been placed adjacent to the desired treatment area, positioning mechanisms may be deployed, if so provided. As discussed above, in some embodiments, the catheter shaft 106 and/or elongate member 110 may include push and/or pull wires to deflect a distal end region 108 of the catheter shaft 106 and/or a distal end region 112 of the elongate member 110. In some instances, the modulation system 100 may be structured such that an operator may have the ability to deflect the catheter shaft 106 and/or elongate member 110 such that the force with which the ablation electrodes 114 contact the vessel wall 104 may be controlled.

In some instances, multiple treatments may be used to achieve the desired tissue modulation. In some instances, the catheter shaft 106 and/or elongate member 110 may be rotated and additional ablation can be performed at multiple locations around the circumference of the vessel 102. The number of times the catheter shaft 106 and/or elongate member 110 is rotated at a given longitudinal location may be determined by the number and size of the ablation electrodes 114 on the distal end region 112. Once a particular location has been ablated, it may be desirable to perform further ablation procedures at different longitudinal locations. If necessary, the catheter shaft 106 and/or elongate member 110 may be rotated to perform ablation around the circumference of the vessel 102 at each longitudinal location. This process may be repeated at any number of longitudinal locations desired. In some instances, the treatment may be performed in a helical pattern such that each treatment region is longitudinally and radially spaced from the adjacent treatment region.

Figure 3:
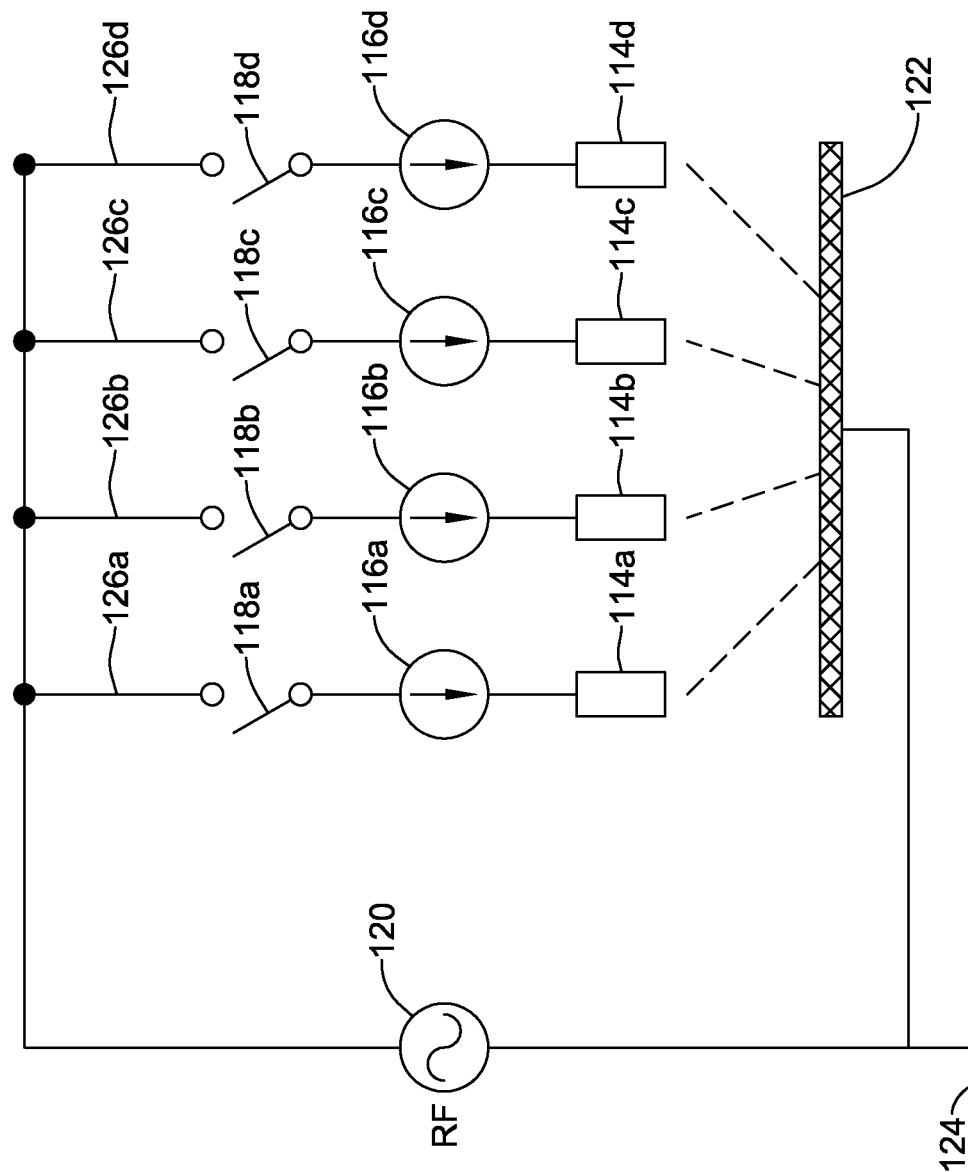
FIG. 3 is a schematic of the electrical connections of an illustrative renal nerve modulation system.

Turning now to FIG. 3, the ablation electrodes 114 may be connected to a control unit 120 or to separate control units by electrical conductors 126a, 126b, 126c, 126d (collectively 126). While the electrical conductors 126 are illustrated as connecting to the control unit 120 by a single line, it is contemplated that the conductors 126a, 126b, 126c, 126d may each be separately connected to the control unit 120, if so desired. Control unit 120 may provide power for operating the electrodes 114 as well as provide control logic for controlling the energy supplied to the electrodes 114. In some instances, an RF generator and a control unit may be supplied separately. As will be explained in more detail below, the control unit 120 may apply power to all electrodes 114 simultaneously with a single RF power source at the beginning of the ablation and switch on/off each electrode 114 based on ablation response. It is further contemplated that power may be delivered to a specific electrode or electrodes if so desired. Due to the nature of renal denervation, each ablation electrode 114 may require a small amount of power, for example, less than 10 Watts (W). A common RF generator design may have a maximum output of 50 to 75 W without any technical issues.

The first electrical conductor 126a may be provided with an electrical switch 118a and a current sensing circuit 116a. The electrical switch 118a may be selectively opened and closed to complete the electrical circuit. The current sensing circuit 116a may include a small value resistor (such as, but not limited to 1 ohm) and one or more amplifiers. Another example of a current sensing circuit may include a current sensing coil and one or more amplifiers. The current sensing circuit may measure the current to the electrode 114a and may also be used to calculate the impedance between the electrode 114a and the ground pad electrode 122. The calculated impedance may be used as a contact indicator (for example, whether or not the electrode 114a is contacting the vessel wall 104) as well as an indication of ablation progress. In general, the resistance of the surrounding tissue may decrease as the temperature of the tissue increases until a point where the tissue begins to denature or irreversibly change, for example, at approximately 50-60° C. Once the tissue has begun to denature the resistance of the tissue may increase. As the target tissue is ablated, the change in impedance may be analyzed to determine how much tissue has been ablated. The power level and duration of the ablation may be adjusted accordingly based on the impedance of the tissue. Electrical conductors 126b, 126c, 126d may also include electrical switches 118b, 118c, 118d and current sensing circuits 116b, 116c, 116d. The electrical switches 118b, 118c, 118d and current sensing circuits 116b, 116d, 116d may be similar in form and function to electrical switch 118a and current sensing circuit 116a previously discussed.

While not explicitly shown, the ablation electrodes 114 may each include a temperature sensor, such as, but not limited to a thermistor or thermocouple, positioned adjacent to the electrode. The temperature sensor may measure the temperature response of the adjacent tissue during the ablation procedure. The temperature response may also be used to monitor the progress of the ablation procedure (for example, temperature may be used as an indication of lesion size).

Figure 4:
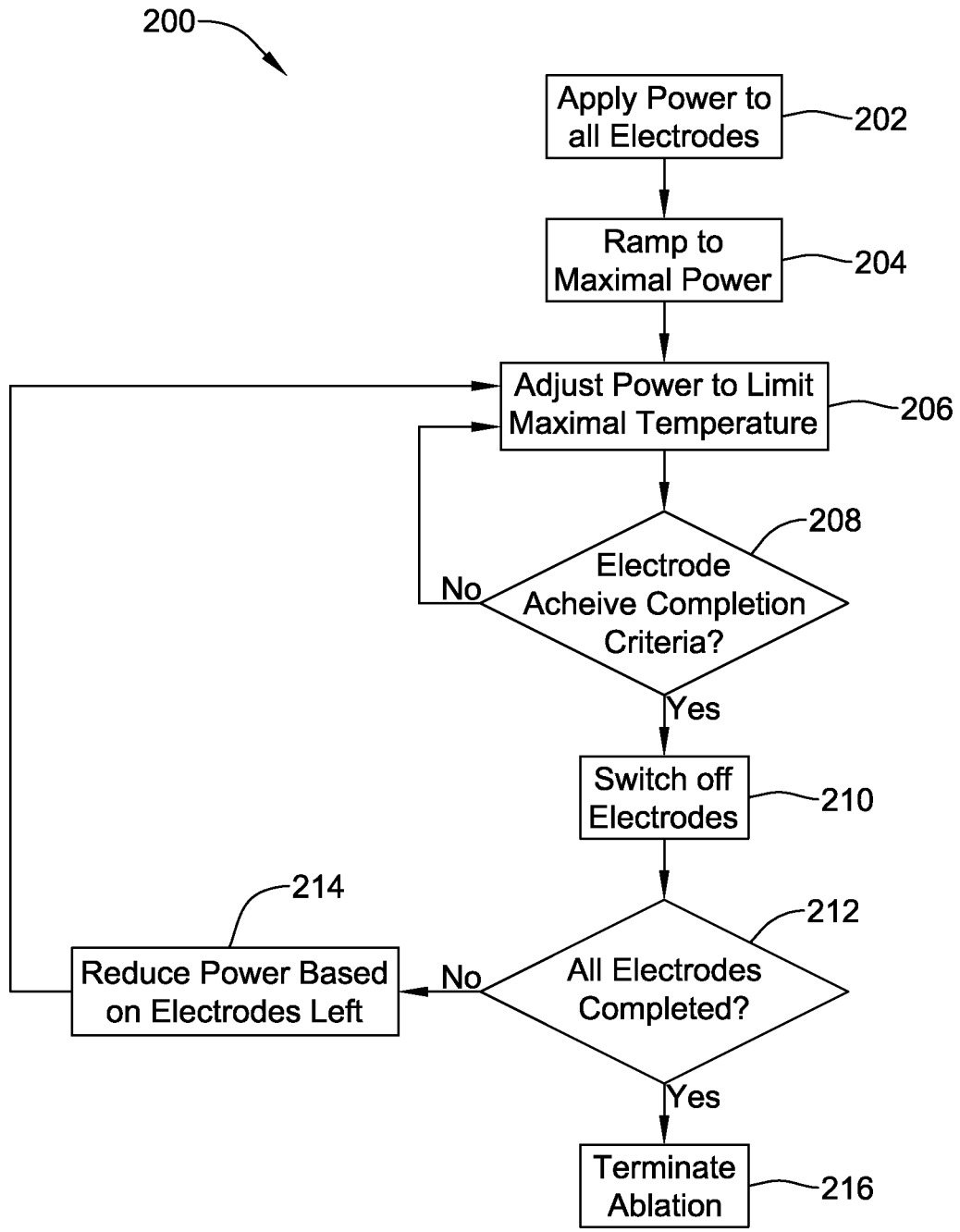
FIG. 4 is a flow chart of an illustrative method of operating a renal nerve modulation system.

The control unit 120 may be configured to monitor the electrical parameters from each electrical conductor 126a, 126b, 126c, 126d as well as the temperature from each temperature sensor. The control unit 120 may control the voltage of the power source to adjust the power supplied to each electrode 114a, 114b, 114c, 114d separately. It is further contemplated the electrical switches 118a, 118b, 118c, 118d may be selectively opened and closed to selectively include or exclude electrodes 114a, 114b, 114c, 114d during the ablation procedure. For example, an individual electrode may be excluded from the ablation procedure during the initial ablation. Power may be delivered to the excluded electrode at a later time, if so desired. This may allow a physician to avoid certain sites due to position or contact. For example an electrode with poor contact, as indicated by an initial impedance reading, may be excluded from the initial ablation. The control unit 120 may include a control algorithm, such as algorithm 200 shown in FIG. 4, for determining how much power should be applied to each electrode 114 and/or for determining when electrodes should be turned on/off.

The control unit 120 may first apply power 202 to all of the electrodes 114a, 114b, 114c, 114d included with the modulation system 100. It is contemplated that the power may be increased or ramped 204 from zero to the maximum power over a predetermined length of time. In some instances, the ramp time may be 5 seconds or less, 10 seconds or less, 15 seconds or less, or greater than 15 seconds as desired. The maximum power may be determined by the number of electrodes 114 and the amount of power supplied to each electrode. For example, a modulation system, such as system 100, including four electrodes 114 each receiving 8 Watts would have a maximum power of 32 Watts. During the ramp time and/or once the maximum power has been reached, the control unit 120 may monitor the electrical parameters from each electrical conductor 126a, 126b, 126c, 126d as well as the temperature from each temperature sensor. If a maximum temperature, for example, but not limited to 65° C., if reached at any one of the electrodes 114a, 114b, 114c, 114d, the power delivered to the electrode that has reached the maximum temperature may be reduced 206. The maximum temperature may be any temperature desired, such as, but not limited, to greater than 50° C. It is contemplated that each of the electrodes 114a, 114b, 114c, 114d may reach a different temperature during the procedure.

The control unit 120 may also monitor the electrical parameters from each electrical conductor 126a, 126b, 126c, 126d as well as the temperature from each temperature sensor to determine if predetermined completion criteria have been met 208. For example, the procedure may be considered complete for a region adjacent an electrode 114 when a target temperature (for example, but not limited to, at least 55° C.) has been sustained for a given time period (for example, but not limited to, at least 25 seconds). The target temperature and time periods are just examples. The target temperature and/or time period may be any temperature or time period desired.

Alternatively, or additionally, the procedure may be considered complete for a region adjacent an electrode 114 when a calculated impedance drops by a predetermined amount (such as, but not limited to 20%). The calculated impedance drop is just an example. The calculated impedance drop may be any impedance drop desired. If an electrode 114 has not met the completion criteria, the control unit 120 may continue to supply/regulate power to and/or monitor the parameters of the electrode 114, as shown in step 206. If an electrode 114 has met the completion criteria, the control unit 120 may turn off the power supply 210 to that particular electrode 114. This may be accomplished via electrical switch 118.

The control unit 120 may also monitor how many electrodes 114 have met the completion criteria 212. If all of the electrodes 114 have not met the completion criteria, the maximum power supplied may be reduced based on the number of electrodes still active in the procedure 214. The control unit 120 may continue to supply/regulate power to and/or monitor the parameters of the electrode 114, as shown in step 206. This procedure may be iterated until all of the electrodes 114 have reached the completion criteria. Once all of the electrodes 114 have met the completion criteria, the procedure is complete 216 and power supply is terminated. It is contemplated that the control algorithm 200 may also terminate the procedure even if the completion criteria have not been met at all of the electrodes 114. For example, ablation may be terminated if the completion criteria have not been met after a predetermined time period. The control algorithm 200 may allow the catheter to create multiple lesions at the same time and to apply power to specific electrodes that need more ablation time or power to achieve the desired tissue modulation. This may short the ablation time and total procedure time. The control algorithm may be further illustrated in example procedures enclosed herein.

Figure 5:
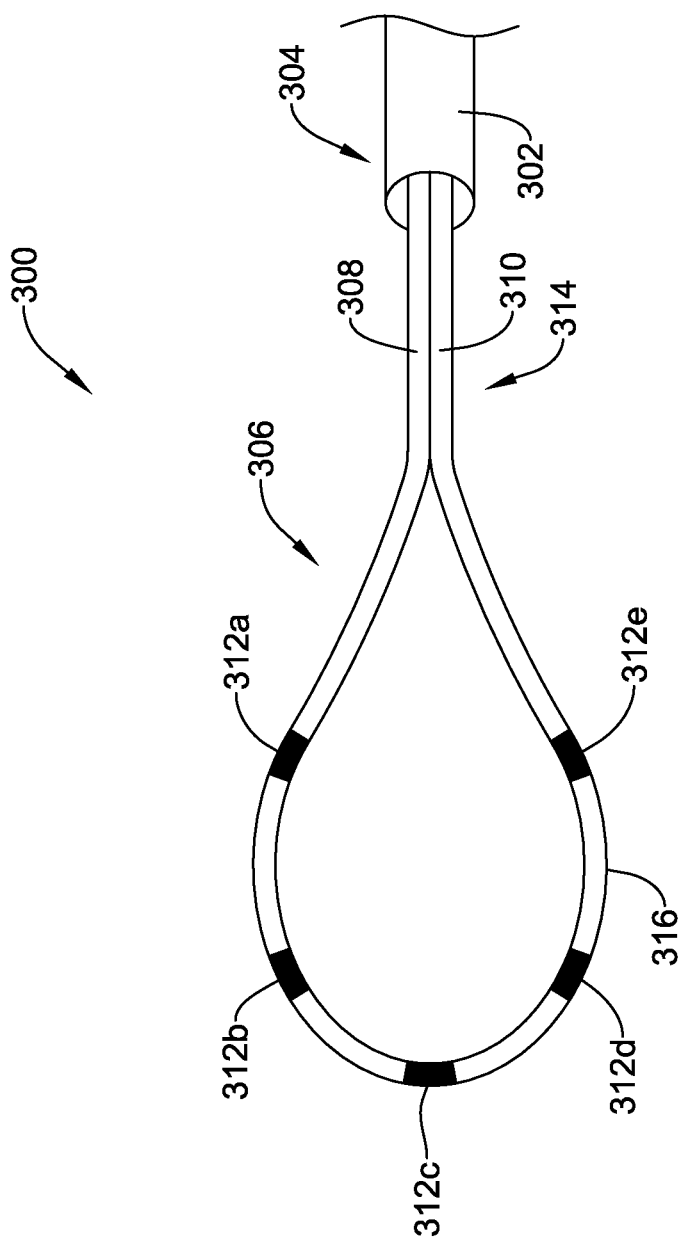
FIG. 5 is another illustrative multi-electrode nerve modulation system.

FIG. 5 illustrates a distal end region of another illustrative renal nerve modulation system 300 that may be similar in form and function to other system disclosed herein. The system 300 may include a catheter shaft 302 having a distal end region 304. The catheter shaft 302 may extend proximally from the distal end region 304 to a proximal end configured to remain outside of a patient's body. The proximal end of the catheter shaft 302 may include a hub attached thereto for connecting other treatment devices or providing a port for facilitating other treatments. It is contemplated that the stiffness of the catheter shaft 302 may be modified to form a modulation system 300 for use in various vessel diameters and various locations within the vascular tree. The catheter shaft 302 may further include one or more lumens extending therethrough. For example, the catheter shaft 302 may include a guidewire lumen and/or one or more auxiliary lumens. The lumens may be configured in any way known in the art. While not explicitly shown, the modulation system 300 may further include temperature sensors/wire, an infusion lumen, radiopaque marker bands, fixed guidewire tip, a guidewire lumen, external sheath and/or other components to facilitate the use and advancement of the system 300 within the vasculature.

The system 300 may include an elongate member 306 extending within a lumen of the catheter shaft 302. In some instances, the elongate member 306 may extend the entire length of the catheter shaft 302 while in other instances, the elongate member 306 may be attached to the catheter shaft 302 adjacent the distal end region 304 thereof. In some instances, the elongate member 306 may include a first portion 308 and a second portion 310. The first and second portions 308, 310 may run side by side or be secured to one another along a proximal region 314, although this is not required. The first and second portions 308, 310 may separate at a distal end of the elongate member 306 to form a looped distal end region 316. The looped distal end region 316 of the elongate member 306 may be configured to be advanced to the desired treatment region within the catheter shaft 302. Once adjacent to the desired treatment region, the distal end region 316 of the elongate member 306 may be advanced distally such that it exits the lumen of the catheter shaft 302. In some instances, the distal end region 316 may be configured to self-expand into a ring while in other instances, actuation mechanisms may be employed to expand the distal end region 316.

The system 300 may include one or more distal ablation electrodes 312a, 312b, 312c, 312e, 312e (collectively 312) positioned adjacent the distal end region 316 of the elongate member 306. The electrodes 312 may be similar in form and function to electrodes 114 described above. While the ablation electrodes 312 are described as a radiofrequency electrode, it is contemplated that other methods and devices for raising the temperature of the nerves may be used, such as, but not limited to: ultrasound, microwave, or other acoustic, optical, electrical current, direct contact heating, or other heating. While the system 300 is illustrated as including five ablation electrodes 312, it is contemplated that the modulation system 300 may include any number of ablation electrodes 312 desired, such as, but not limited to, one, two, three, four, or more. The ablation electrodes 312 may be longitudinally and/or radially and/or circumferentially spaced as desired. The ablation electrodes 312 may be spaced about the distal end region 316, although this is not required. In some instances, the electrodes 312 may be positioned about the distal end region 316 such that not all of the electrodes 312 contact the vessel wall at the same time when the distal end region 316 is in the expanded state. In other instances, the electrodes 312 may be arranged such that all of the electrodes 312 are configured to contact the vessel wall simultaneously when the distal end region 316 is in the expanded state.

While not explicitly shown, the ablation electrodes 312 may also include other structures and/or features associated typically associated with ablation (e.g., thermal ablation) such as a temperature monitoring member, which may take the form of a thermocouple or thermistor. In at least some embodiments, a thermistor including two thermistor wires may be disposed adjacent to one or more of the ablation electrodes 312. In some embodiments, the wires are not physically connected to ablation electrodes 312.

Figure 6:
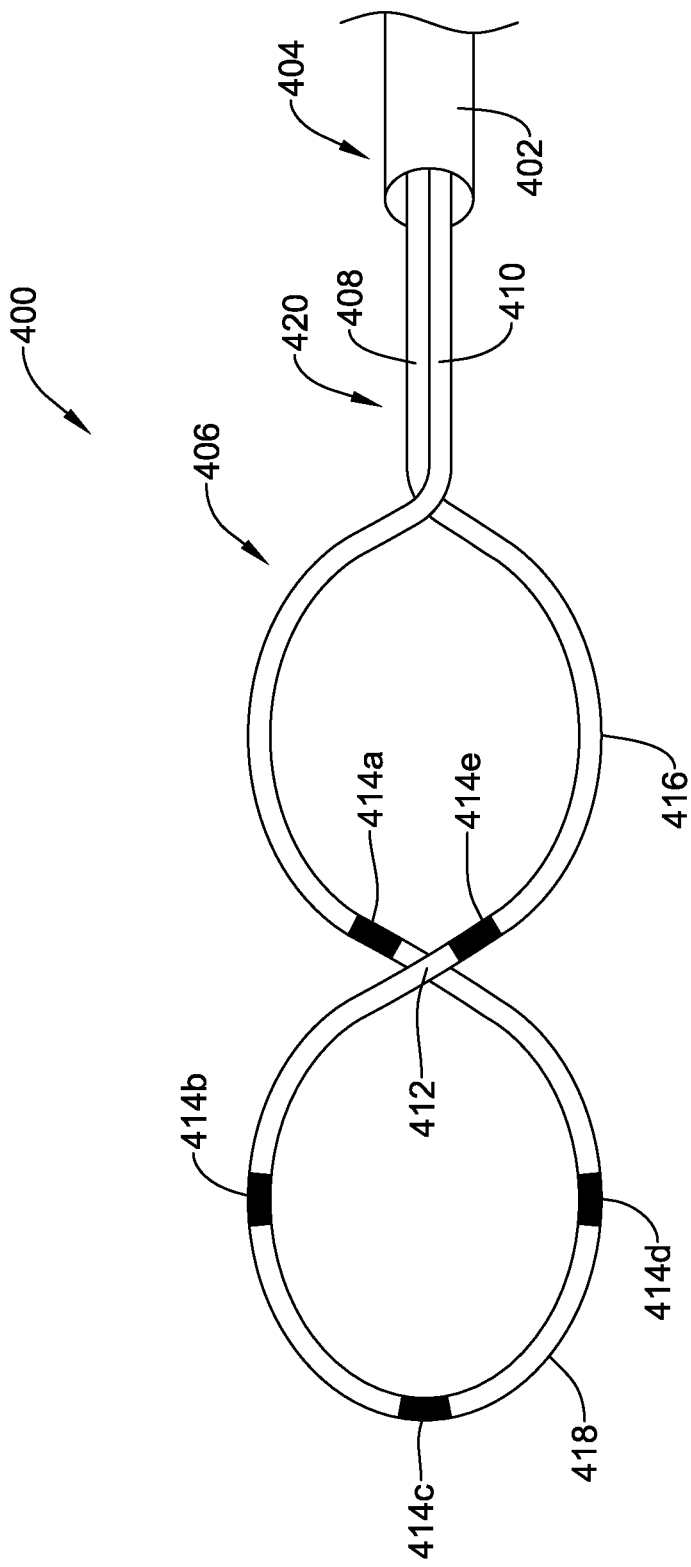
FIG. 6 is another illustrative multi-electrode nerve modulation system.

FIG. 6 illustrates a distal end region of another illustrative renal nerve modulation system 400 that may be similar in form and function to other system disclosed herein. The system 400 may include a catheter shaft 402 having a distal end region 404. The catheter shaft 402 may extend proximally from the distal end region 404 to a proximal end configured to remain outside of a patient's body. The proximal end of the catheter shaft 402 may include a hub attached thereto for connecting other treatment devices or providing a port for facilitating other treatments. It is contemplated that the stiffness of the catheter shaft 402 may be modified to form a modulation system 400 for use in various vessel diameters and various locations within the vascular tree. The catheter shaft 402 may further include one or more lumens extending therethrough. For example, the catheter shaft 402 may include a guidewire lumen and/or one or more auxiliary lumens. The lumens may be configured in any way known in the art. While not explicitly shown, the modulation system 400 may further include temperature sensors/wire, an infusion lumen, radiopaque marker bands, fixed guidewire tip, a guidewire lumen, external sheath and/or other components to facilitate the use and advancement of the system 400 within the vasculature.

The system 400 may include an elongate member 406 extending within a lumen of the catheter shaft 402. In some instances, the elongate member 406 may extend the entire length of the catheter shaft 402 while in other instances, the elongate member 406 may be attached to the catheter shaft 402 adjacent the distal end region 404 thereof. In some instances, the elongate member 406 may include a first portion 408 and a second portion 410. The first and second portions 408, 410 may run side by side or be secured to one another along a proximal region 420, although this is not required. The first and second portions 408, 410 may separate to form a first looped region 416 and a second looped region 418 adjacent a distal end of the elongate member 406. The first portion 408 may cross over the second portion 410 at an intersection point 412 to define the first and second looped regions 416, 418. The looped regions 416, 418 of the elongate member 406 may be configured to be advanced to the desired treatment region within the catheter shaft 402. Once adjacent to the desired treatment region, the looped regions 416, 418 of the elongate member 406 may be advanced distally such that it exits the lumen of the catheter shaft 402. In some instances, the looped regions 416, 418 may be configured to self-expand into a two looped structure while in other instances, actuation mechanisms may be employed to expand the distal end region 416.

The system 400 may include one or more distal ablation electrodes 414a, 414b, 414c, 414d, 414e (collectively 414) positioned adjacent the distal end region 416 of the elongate member 406. The electrodes 414 may be similar in form and function to electrodes 114 described above. While the ablation electrodes 414 are described as a radiofrequency electrode, it is contemplated that other methods and devices for raising the temperature of the nerves may be used, such as, but not limited to: ultrasound, microwave, or other acoustic, optical, electrical current, direct contact heating, or other heating. While the system 400 is illustrated as including five ablation electrodes 414, it is contemplated that the modulation system 400 may include any number of ablation electrodes 414 desired, such as, but not limited to, one, two, three, four, or more. The ablation electrodes 414 may be longitudinally and/or radially and/or circumferentially spaced as desired. The ablation electrodes 414 may be spaced about the looped regions 416, 418, although this is not required. In some instances, the electrodes 414 may be positioned about the distal end region 416 such that not all of the electrodes 414 contact the vessel wall at the same time when the looped regions 416, 418 are in the expanded state. In other instances, the electrodes 414 may be arranged such that all of the electrodes 414 are configured to contact the vessel wall simultaneously when the looped regions 416, 418 are in the expanded state.

While not explicitly shown, the ablation electrodes 414 may also include other structures and/or features associated typically associated with ablation (e.g., thermal ablation) such as a temperature monitoring member, which may take the form of a thermocouple or thermistor. In at least some embodiments, a thermistor including two thermistor wires may be disposed adjacent to one or more of the ablation electrodes 414. In some embodiments, the wires are not physically connected to ablation electrodes 414.

The materials that can be used for the various components of devices/systems 12, 100, 300, 400 (and/or other medical devices disclosed herein) may include those commonly associated with medical devices. For simplicity purposes, the following discussion makes reference to device 12. However, this is not intended to limit the devices and methods described herein, as the discussion may be applied to other similar medical devices disclosed herein.

Device 12 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of device 12 may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of device 12 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 12 to achieve the same result.

In some embodiments, a degree of Magnetic Resonance Imaging (MRI) compatibility is imparted into device 12. For example, device 12 or portions thereof may be made of a material that does not substantially distort the image and create substantial artifacts (i.e., gaps in the image). Certain ferromagnetic materials, for example, may not be suitable because they may create artifacts in an MRI image. Device 12 or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for device 12 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Example 1

An example of control algorithm 200 is provided herein. This example is merely exemplary and is not intended to limit the control algorithm to the example scenario provided. It is contemplated the times, temperature, impedance drops, power levels, and number of electrodes active will vary from procedure to procedure. A modulation system including four electrodes is provided. The electrodes are positioned adjacent to a desired treatment region. A maximum temperature for the system is set at 65° C. At the start of the modulation procedure (time (t)=0), power is delivered to all four electrodes with a 5 second ramp to a power limit of 32 Watts. Each electrode receives 8 Watts. At t=5 seconds, power is being delivered at a full 32 Watts. The temperature of a first, second, and third electrodes reaches 55° C. at t=5 seconds. The fourth electrode reaches 55° C. at t=15 seconds. The impedance of each electrode drops by more than 20%. At t=30 seconds the first, second, and third electrodes achieve the ablation criteria (for example, T=55° C. for at least 25 seconds). The first, second, and third electrodes are turned off. The total power supplied to system is reduced to 8 Watts, the maximal power for one electrode. At t=40 seconds, the fourth electrode achieves the ablation criteria (for example, T=55° C. for at least 25 seconds) and is turned off. The ablation procedure is terminated.

Example 2

Another example of control algorithm 200 is provided herein. This example is merely exemplary and is not intended to limit the control algorithm to the example scenario provided. It is contemplated the times, temperature, impedance drops, power levels, and number of electrodes active will vary from procedure to procedure. A modulation system including four electrodes is provided. The electrodes are positioned adjacent to a desired treatment region. A maximum temperature for the system is set at 65° C. At the start of the modulation procedure (time (t)=0), power is delivered to all four electrodes with a 5 second ramp to a power limit of 32 Watts. Each electrode receives 8 Watts. At t=5 seconds, the temperature of the first electrode reaches 65° C. and the total power is reduces to 24 Watts, each electrode receiving 6 Watts. The temperature of the second and third electrodes reaches 55° C. and the temperature of the fourth electrode remains at 45° C. because 6 Watts is not enough to bring the temperature to 55° C. The impedance of the first, second, and third electrodes drops by more than 20%. The impedance of the fourth electrode drops by 5%. At t=30 seconds the first, second, and third electrodes achieve the ablation criteria (for example, T=55° C. for at least 25 seconds). The first, second, and third electrodes are turned off. The total power supplied to system is reduced to 6 Watts for the fourth electrode. The system may then adjust the power to the fourth electrode to approximately 8 Watts. At t=32 seconds, the fourth electrode reaches 55° C. and impedance drops by more than 20%. At t=57 seconds, the fourth electrode achieves the ablation criteria (for example, T=55° C. for at least 25 seconds) and is turned off. The ablation procedure is terminated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A nerve modulation system, comprising:
   an elongate member having a proximal end and a distal end region;
   two or more electrodes positioned adjacent to the distal end region of the elongate member;
   a ground pad;
   a control unit in electrical communication with each of the two or more electrodes, the control unit positioned adjacent to the proximal end of the elongate shaft; and
   an electrical conductor extending between each of the two or more electrodes and the control unit, each electrical conductor comprising an electrical switch and a current sensing circuit configured to measure the current to each of the two or more electrodes and to calculate an impedance between each of the two or more electrodes and the ground pad,
   wherein the current sensing circuit includes a resistor and one or more amplifiers or wherein the current sensing circuit includes a current sensing coil and one or more amplifiers, and
   wherein the control unit includes a control algorithm configured to selectively control power applied to each of the two or more electrodes.

2. The nerve modulation system of claim 1, wherein the control unit applies the power to the two or more electrodes simultaneously.

3. The nerve modulation system of claim 1 wherein the control unit applies power to fewer than all of the two or more electrodes.

4. The nerve modulation system of claim 1, further comprising a temperature sensor disposed adjacent to each of the two or more electrodes.

5. The nerve modulation system of claim 1, wherein the control unit is configured to monitor electrical parameters of each circuit created by the control unit, each of the two or more electrodes and the ground pad.

6. The nerve modulation system of claim 5, wherein the control unit is configured to terminate ablation upon reaching a predetermined temperature or other electrical parameter.

7. The nerve modulation system of claim 1, wherein the current sensing circuit includes the resistor and one or more amplifiers.

8. The nerve modulation system of claim 1, wherein the current sensing circuit includes the current sensing coil and one or more amplifiers.

9. A nerve modulation system, comprising:
   an elongate member having a proximal end and a distal end region;
   two or more electrodes positioned adjacent to the distal end region of the elongate member;
   a ground pad;
   a control unit in electrical communication with each of the two or more electrodes, the control unit configured to supply electrical energy to activate the two or more electrodes; and
   an electrical conductor extending between each of the two or more electrodes and the control unit, each electrical conductor comprising an electrical switch and a current sensing circuit configured to measure the current to each of the two or more electrodes and to calculate an impedance between each of the two or more electrodes and the ground pad,
   wherein the current sensing circuit includes a resistor and one or more amplifiers or wherein the current sensing circuit includes a current sensing coil and one or more amplifiers,
   wherein the control unit includes a control algorithm configured to selectively control power applied to each of the two or more electrodes, and
   wherein the control unit is configured to monitor electrical parameters of each circuit created by the control unit, each of the two or more electrodes and the ground pad.

10. The nerve modulation system of claim 9, wherein the control unit applies the power to the two or more electrodes simultaneously.

11. The nerve modulation system of claim 9, wherein the control unit applies power to fewer than all of the two or more electrodes.

12. The nerve modulation system of claim 9, further comprising a temperature sensor disposed adjacent to each of the two or more electrodes.

13. The nerve modulation system of claim 9, wherein the control unit is configured to terminate ablation upon reaching a predetermined temperature or other electrical parameter.

14. The nerve modulation system of claim 9, wherein the current sensing circuit includes the resistor and one or more amplifiers.

15. The nerve modulation system of claim 9, wherein the current sensing circuit includes the current sensing coil and one or more amplifiers.

16. The nerve modulation system of claim 9, wherein the control algorithm is configured to control a level of the power and a duration of the power that is applied to each of the two or more electrodes based on the impedance that is calculated.

17. A nerve modulation system, comprising:
    an elongate member having a proximal end and a distal end region;
    three or more electrodes positioned adjacent to the distal end region of the elongate member;
    a ground pad;
    a control unit in electrical communication with each of the three or more electrodes, the control unit configured to supply electrical energy to activate the three or more electrodes; and
    an electrical conductor extending between each of the three or more electrodes and the control unit, each electrical conductor comprising an electrical switch and a current sensing circuit configured to measure the current to each of the three or more electrodes and to calculate an impedance between each of the three or more electrodes and the ground pad,
    wherein the current sensing circuit includes a resistor and one or more amplifiers or wherein the current sensing circuit includes a current sensing coil and one or more amplifiers, wherein the control unit includes a control algorithm configured to selectively control power applied to each of the three or more electrodes, and wherein the control unit is configured to apply the power to the three or more electrodes simultaneously or is configured to apply the power to fewer than all of the three or more electrodes.

18. The nerve modulation system of claim 17, wherein the current sensing circuit includes the resistor and one or more amplifiers.

19. The nerve modulation system of claim 17, wherein the current sensing circuit includes the current sensing coil and one or more amplifiers.

20. The nerve modulation system of claim 17, wherein the control algorithm is configured to control a level of the power and a duration of the power that is applied to each of the three or more electrodes based on the impedance that is calculated.

* * * * *